(12) United States Patent
Takikawa (10) Patent No.: US 6,321,643 B1
(45) Date of Patent: Nov. 27, 2001

(54) DEFECTIVE-PORTION MARKING METHOD, DEFECTIVE-PORTION MARKING APPARATUS, AND BUNDLING APPARATUS

(75) Inventor: Katsunobu Takikawa, Hachioji (JP)

(73) Assignee: Takikama Engineering Co., Ltd., Tokyo (JP)

( * ) Notice: Subject to any disclaimer, the term of this patent is extended or adjusted under 35 U.S.C. 154(b) by 0 days.

(21) Appl. No.: 09/452,738

(22) Filed: Dec. 1, 1999

(30) Foreign Application Priority Data

Jun. 10, 1999 (JP) .................................. 11-163319

(51) Int. Cl.$^7$ ............................ B65B 27/10; B65H 63/00
(52) U.S. Cl. .................................. 100/2; 53/54; 53/399; 53/589; 100/8; 100/10; 100/27
(58) Field of Search .................................. 100/1, 2, 8, 9, 100/10, 13, 14, 27; 53/399, 589, 441, 556, 54

(56) References Cited

U.S. PATENT DOCUMENTS

| 3,015,916 | * | 1/1962 | Denton ................. 100/10 X |
| 3,217,461 | * | 11/1965 | Wheelock ................. 100/2 |
| 3,288,055 | * | 11/1966 | Vellrath ................. 100/10 X |
| 3,393,633 | * | 7/1968 | Hoffman ................. 100/2 |
| 4,312,173 |   | 1/1982 | Killermann . |
| 4,502,905 |   | 3/1985 | Jung et al. . |
| 5,727,454 |   | 3/1998 | Takikawa . |

FOREIGN PATENT DOCUMENTS

| 0 772 207 |   | 10/1996 | (EP) . |
| 2-57516-A | * | 2/1990 | (JP) ......................................... 100/8 |
| 9-202532 |   | 8/1997 | (JP) . |

OTHER PUBLICATIONS

European Search Report, Appln. No. 99 30 9628, Jun. 5, 2001.

* cited by examiner

Primary Examiner—Stephen F. Gerrity
(74) Attorney, Agent, or Firm—Darby & Darby (57) ABSTRACT

A defective-portion marking method and defective-portion marking apparatus which can put a mark all around a long body (1), ensure easy removal of the mark, and eliminate the need for securely joining both ends of a line-like elastic body (2') into a ring shape. A long elastic body (2) supplied from an elastic-body feeding mechanism (6) is held by a pair of pinchers (51), and as the pinchers are turned by a rotary mechanism (52), the long elastic body is wound on a holder (3). Then, the contact pin (41) of an entwining mechanism (4) moves forward to entwine the long elastic body, which is cut to the line-like elastic body by a cutter (516) provided on one of the pinchers. The contact pin moves further to free the line-like elastic body from the holder so that the line-like elastic body is wound around the long body at a defective portion or in a vicinity thereof due to its own elasticity.

5 Claims, 10 Drawing Sheets

DEFECTIVE-PORTION MARKING METHOD, DEFECTIVE-PORTION MARKING APPARATUS, AND BUNDLING APPARATUS

BACKGROUND OF THE INVENTION

1. Field of the Invention

The present invention relates to a method and apparatus for marking positions of defective portions on a long elongated body such as an electric wire, a pipe, or a hose, and a bundling apparatus for bundling a plurality of long bodies.

This application is based on patent application number Hei 11-163319 filed in Japan, the contents of which are incorporated herein by reference.

2. Description of the Related Art

Long bodies, such as electric wires, various kinds of pipes, hoses of various kinds of materials, and rods or lines of steel, glass, plastic and the like, are being manufactured actively. At the site where such long bodies are manufactured, defective portions like scratches present on the surface of a manufactured long body are detected by a specific method. In a case of electric wires or the like, for example, an ultrasonic probing apparatus, a detecting apparatus using an excess current or the like, are used to detect scratches on the surface of such a wire.

When a defective portion is detected by such a method, the production line is stopped to check the defective portion or the position thereof is automatically recorded in a computer. Mere recording of a defective portion in a computer without marking it on a product itself makes it hard to find the defective portion in such a case where the product is used after cutting out the defective portion.

Conventionally, therefore, some methods have been used to mark the position of a defective portion on a product itself. The conventional marking methods include a scheme of spraying ink on the surface of a product and a scheme of sticking a seal on a product.

The conventional marking methods however have the following shortcomings.

The scheme of spraying ink often sprays ink while a long body is running to be wound up, and faces such a problem that the ink gets thinner as the running speed becomes higher. If the actual inspection of a marked portion proves the determination of the defective portion wrong, the marking should be removed. In the case of sprayed ink, however, it is hard to remove the marking. Further, because only a specific portion on the outer surface of a long body is marked, it is difficult to spray ink all around the long body. In this case, it is not easy to find a marking made on a specific portion and the marking may be missed.

With regard to the scheme of attaching a seal, depending on the surface condition of the long body, it may be difficult to attach a seal on a long body. If an easily separable seal is used to facilitate the later removal of the seal, the seal may be separated at the time of transportation or the like, so that the position of the associated defective portion will not be located. Like in the case of the ink spraying method, it is difficult to put a marking all around a long body, thus making it hard to find the marked portion.

As a solution of the above problems, a scheme of making a mark by winding a ring-shaped elastic body like a rubber band on a long body is disclosed in Japanese Patent Application, First Publication No. Hei 9-202532. This publication discloses the structure which prepares a ring-like elastic body by securely joining both ends of a line-like elastic body of a given length and feeding it.

This structure, however, has the disadvantage of the structure for securely joining both ends of a line-like elastic body becoming large. In addition, the strength of the joined portion should be considered. In other words, if the elasticity of the ring-like elastic body is increased to enhance the winding strength, the secured portion may be cut. Further, to remove a marking, the ring-like elastic body should be cut with scissors or the like. When a long body is cut, the ring-like elastic body can be removed through the cut portion. But, in a case where the actual inspection of a marked portion proves the determination of the defective portion wrong or a long body cannot be cut due to some restriction in the production process, the ring-like elastic body still has to be cut with scissors or the like, which is troublesome.

Accordingly, it is a primary object of the present invention to provide a defective-portion marking method and defective-portion marking apparatus which can reliably put a mark on a long body even when the running speed of the long body becomes high, can easily remove the mark later when needed, can prevent separation of a mark at the time of transportation or the like, can put a mark all around a long body, thus facilitating later locating of the marked portion, and eliminate the need for securely joining both ends of a line-like elastic body.

It is another object of this invention to provide a bundling apparatus which makes untying the bundled long bodies easier.

SUMMARY OF THE INVENTION

To achieve the first object, a defective-portion marking method according to this invention comprises the steps of holding a line-like elastic body having a free length shorter than a circumference of the long body in an entwined state in such a way that the line-like elastic body forms a turn greater than the circumference of the long body; and then releasing the line-like elastic body to permit the line-like elastic body to contract by an elasticity thereof, thereby entwining and winding the line-like elastic body around the long body at a defective portion or in a vicinity thereof.

A defective-portion marking apparatus according to this invention comprises a holder for holding a line-like elastic body having a free length shorter than a circumference of the long body in an entwined state in such a way that the line-like elastic body forms a turn greater than the circumference of the long body; and an entwining mechanism for freeing the line-like elastic body of holding by the holder to permit the line-like elastic body to contract by the elasticity thereof, thereby entwining and winding the line-like elastic body around the long body at a defective portion or in a vicinity thereof.

It is preferable that the defective-portion marking apparatus further comprises a cutter for cutting a long elastic body whose length is twice a length of the line-like elastic body or greater at a predetermined length, providing the line-like elastic body; and an elastic-body feeding mechanism for feeding the long elastic body to the cutter.

It is also preferable that in the defective-portion marking apparatus, the holder holds the line-like elastic body stretched in one or more turns along a circumference greater than the circumference of the long body.

To achieve the second object, a bundling apparatus for bundling a plurality of long bodies according to this invention comprises a holder for holding a line-like elastic body having a free length shorter than a circumference of a bundle of a plurality of long bodies in an entwined state in such a way that the line-like elastic body forms a turn greater than the circumference of the bundle of long bodies; and a freeing mechanism for freeing the line-like elastic body of holding by the holder to permit the line-like elastic body to contract by the elasticity thereof, thereby winding the line-like elastic body around the bundle of long bodies.

DETAILED DESCRIPTION OF THE PREFERRED EMBODIMENTS

Preferred embodiments of the present invention will be described below.

Figure 1:
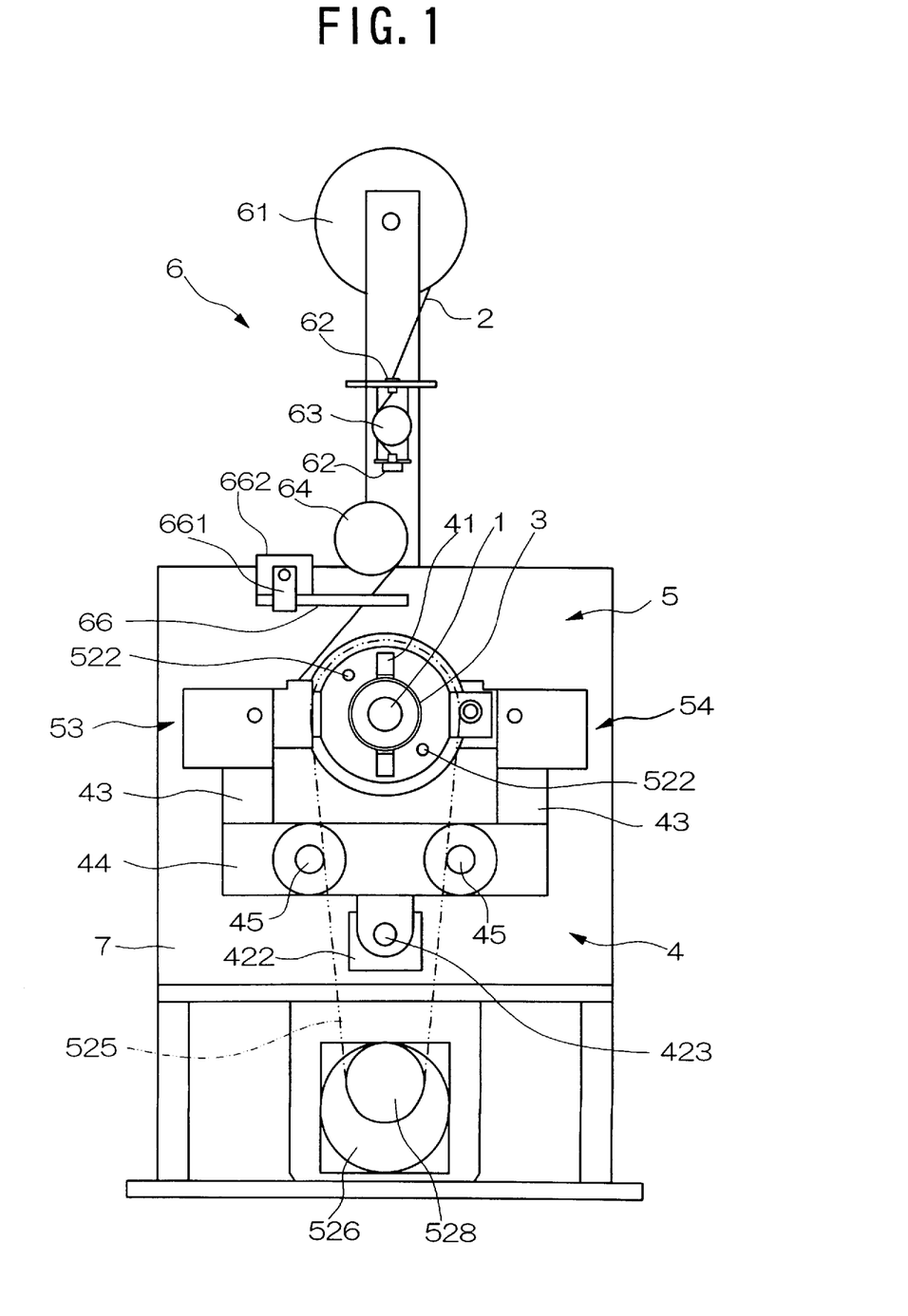
FIG. 1 is a front view exemplifying the schematic structure of a defective-portion marking apparatus according to this invention.

A defective-portion marking apparatus shown in FIG. 1 makes a marking on a long body 1 by holding a line-like elastic body (not shown in FIG. 1) having a free length shorter than the circumference of the long body 1 in an entwined state in such a way that the line-like elastic body forms a turn greater than the circumference of the long body 1, and freeing the line-like elastic body to permit the line-like elastic body to contract by the elasticity thereof, thereby winding the line-like elastic body around the long body 1 at a defective portion or in the vicinity thereof. The apparatus shown in FIG. 1 comprises a holder 3 for holding the line-like elastic body in an entwined sate in such a way that the line-like elastic body forms a turn greater than the circumference of the long body 1, and an entwining mechanism 4 for freeing the line-like elastic body of holding by the holder 3 to permit the line-like elastic body to contract by the elasticity thereof, thereby entwining and winding the line-like elastic body around the long body 1 at a defective portion or in the vicinity thereof. This apparatus further includes a winding mechanism 5 for winding the line-like elastic body around the holder 3 and an elastic-body feeding mechanism 6 for feeding a long elastic body 2, of which the line-like elastic body is made, to the winding mechanism 5.

Figure 2:
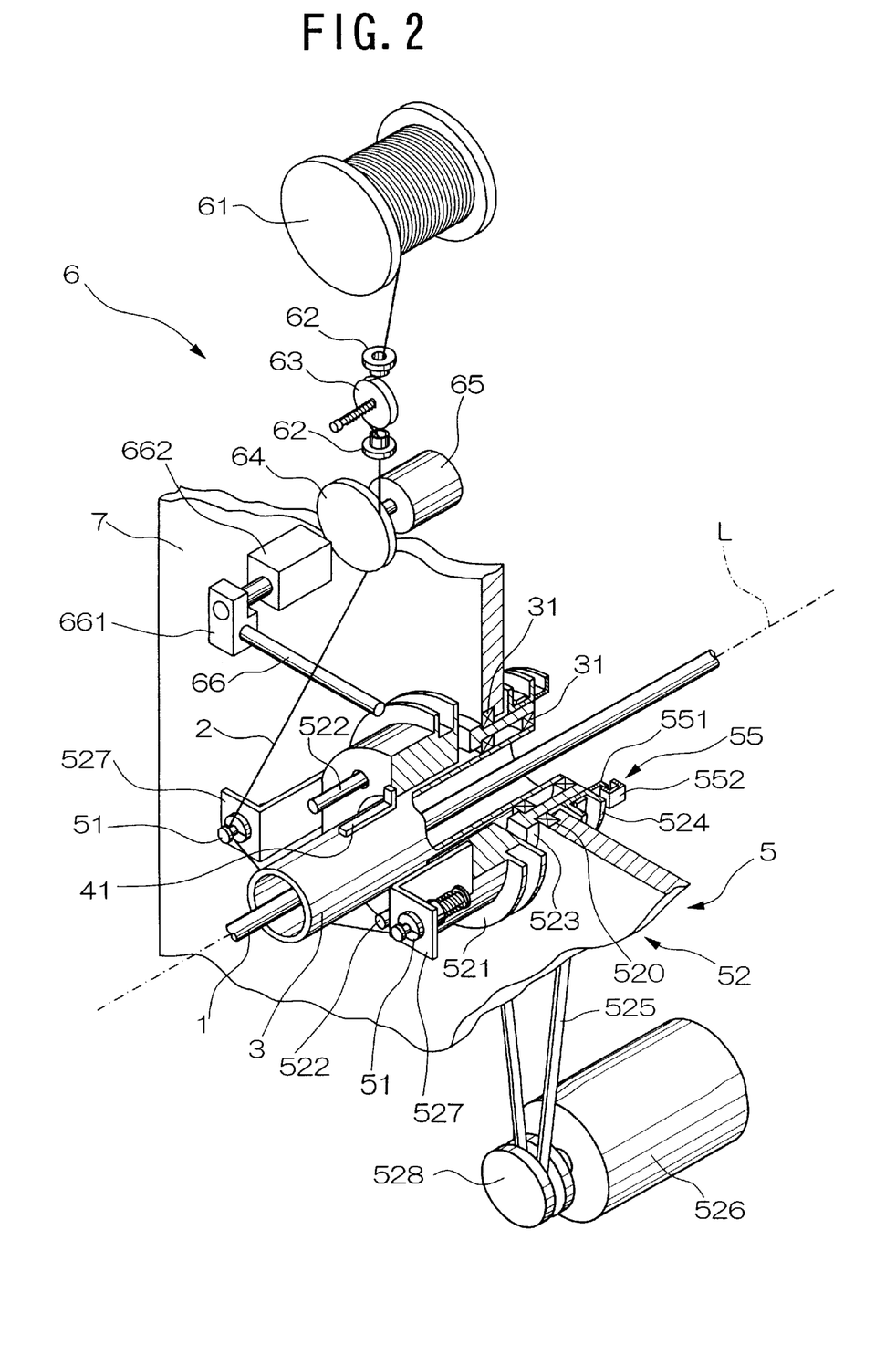
FIG. 2 is a perspective view illustrating the schematic structures of a holder, a winding mechanism, an elastic-body feeding mechanism, etc. in the apparatus shown in FIG. 1, partly in cross-section for easier understanding of the structures.

Referring to FIGS. 1 and 2, the structures of the holder 3, the winding mechanism 5 and the elastic-body feeding mechanism 6 will be discussed below. FIG. 2 is a perspective view illustrating the schematic structures of the holder 3, the winding mechanism 5, the elastic-body feeding mechanism 6, etc. in the apparatus shown in FIG. 1, partly in cross-section for easier understanding of the structures.

The holder 3 is cylindrical as shown in FIGS. 1 and 2 in this embodiment. The holder 3 is secured to a vertical base plate 7. The long body 1 to be marked runs along a running path L set on the center axis of the holder 3 as shown in FIG. 2. In the following description, the running direction of the long body 1 is simply called the "running direction", the side toward which the long body 1 moves forward is called the "front" and the opposite side is called the "rear".

The line-like elastic body is wound around the cylindrical holder 3 by the winding mechanism 5 and is entwined on the long body 1 by the entwining mechanism 4. The details of the winding mechanism 5 will now be described referring to FIGS. 1 and 2.

The winding mechanism 5 comprises a pair of pinchers 51 for holding the long elastic body 2 at its distal end and at a position apart by a predetermined length from that distal end, and a rotary mechanism 52 for integrally turning the pinchers 51 to wind a portion of the predetermined length from the distal end of the long elastic body 2 around the holder 3.

Figure 3A:
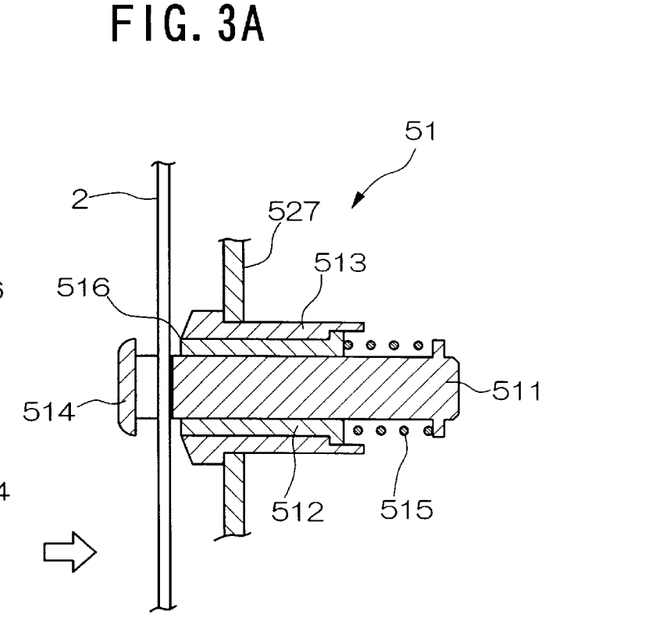
FIG. 3A is a cross-sectional view showing the schematic structure of a pincher in the winding mechanism shown in FIGS. 1 and 2.
Figure 3B:
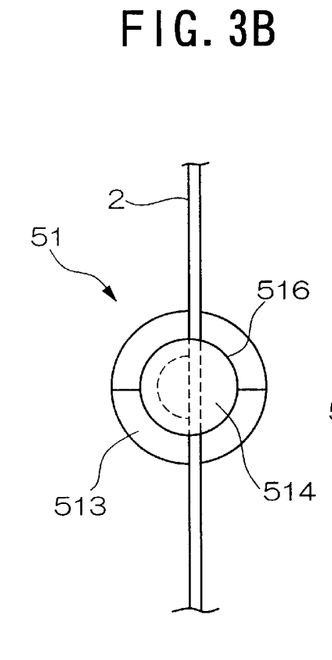
FIG. 3B is a view of the pincher in FIG. 3A along the direction of the arrow.
Figure 3C:
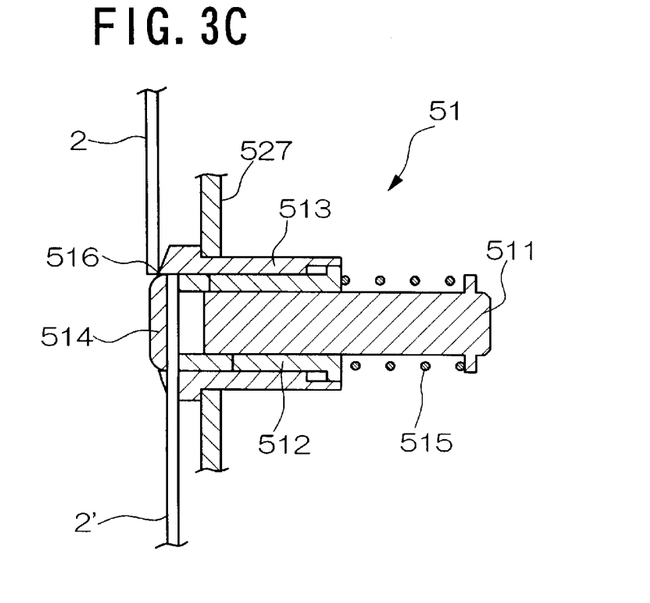
FIG. 3C is a cross-sectional view showing the schematic structure of a pincher in the winding mechanism shown in FIGS. 1 and 2 at the stage that a long elastic body is cut.

The structure of the pincher 51 will now be explained with reference to FIG. 2 and FIGS. 3A to 3C. FIGS. 3A to 3C show the structure of the pincher 51 in the winding mechanism 5 shown in FIGS. 1 and 2. FIGS. 3A and 3C are cross-sectional views and FIG. 3B is a view of the pincher 51 in FIG. 3A along the direction of the arrow. As shown in FIGS. 3A to 3C, the pincher 51 is comprised of a pinching rod 511, a movable sleeve 512 in which the pinching rod 511 is inserted, and a fixed sleeve 513 in which the movable sleeve 512 is fitted.

The whole pinching rod 511 is a nearly round rod. The pinching rod 511 has a notch formed in its distal end so as to have a semicircular cross section. As shown in FIGS. 3A to 3C, a large-diameter end plate 514 is provided at the distal end of the pinching rod 511.

The movable sleeve 512 is a cylindrical member whose inside diameter matches the outside diameter of the pinching rod 511. The fixed sleeve 513 is a nearly cylindrical member whose inside diameter matches the outside diameter of the movable sleeve 512. The movable sleeve 512 is movable in the axial direction while being sandwiched between the pinching rod 511 and the fixed sleeve 513.

A flange portion is formed at the rear end portion of the pinching rod 511. A coil spring 515 is so provided as to couple this flange portion to the movable sleeve 512. The elasticity of the coil spring 515 acts to move the pinching rod 511 (backward) in such a manner that the rear end of the pinching rod 511 moves away from the movable sleeve 512.

The long elastic body 2 is to be fitted in the notch at the distal end of the pinching rod 511 as shown in FIG. 3A. When the pinching rod 511 is moved backward by the elasticity of the coil spring 515 in this situation, the long elastic body 2 is held between the end plate 514 and the end face of the movable sleeve 512.

The pincher 51 has a cutter 516 for cutting the long elastic body 2. As shown in FIGS. 3A and 3C, the upper half of the front end face of the fixed sleeve 513 slightly protrudes forward and is tapered. The edge of this tapered surface on the center axis side is a knife edge which serves as the cutter 516.

The long elastic body 2, if simply held between the end plate 14 and the end face of the movable sleeve 512 as mentioned above, is not cut, but if further force is applied to move the pinching rod 511 in the backward direction as will be discussed below, the long elastic body 2 is pressed against the cutter 516 to be cut as shown in FIG. 3C.

Figure 4:
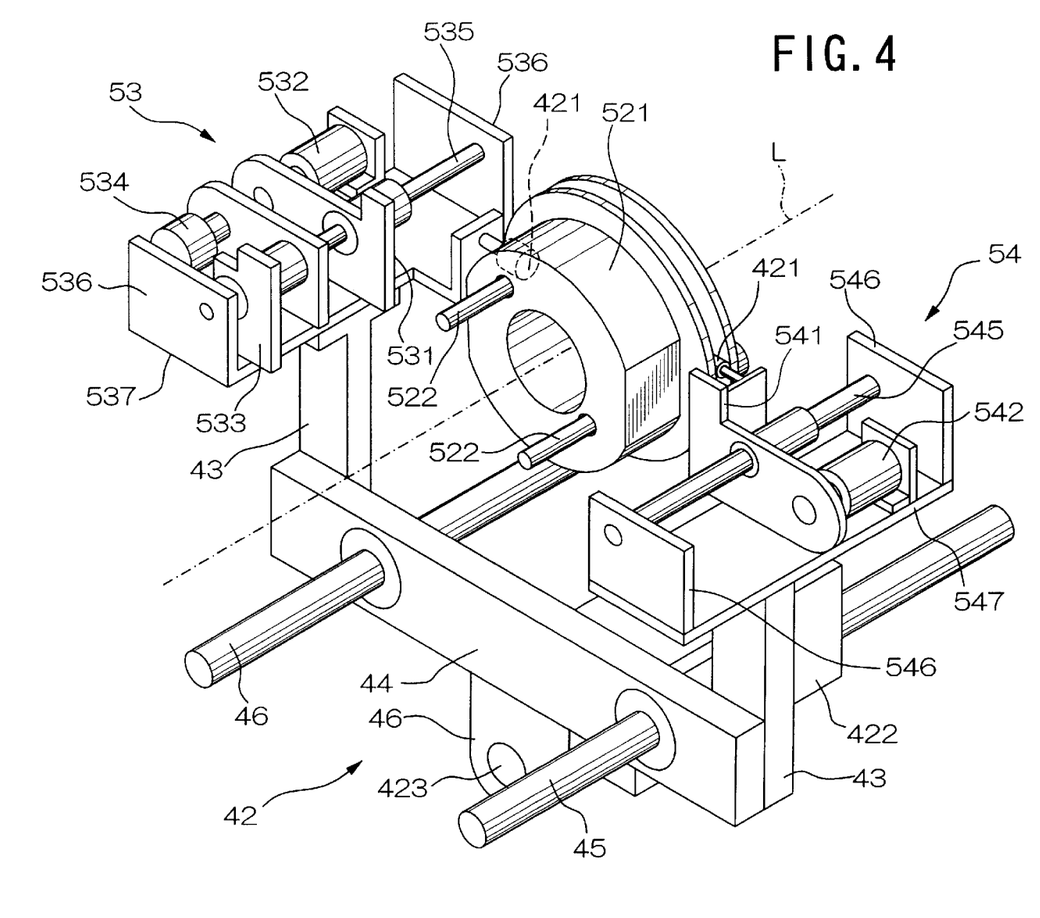
FIG. 4 is a perspective view depicting the schematic structures of pincher drive sections, an entwining mechanism, etc. in the marking apparatus shown in FIG. 1.

The pair of pinchers 51 are driven by a pair of pincher drive sections 53 and 54. Referring to FIG. 4, the structures of the pincher drive sections 53 and 54 will now be discussed. FIG. 4 is a perspective view depicting the pincher drive sections 53 and 54, the entwining mechanism 4, etc. in the defective-portion marking apparatus shown in FIG. 1.

The pincher drive section 53 (hereinafter referred to as "first pincher drive section"), one of the pair of pincher drive sections 53 and 54, is located near the position to which the long elastic body 2 is fed by the elastic-body feeding mechanism 6, and the other pincher drive section 54 (hereinafter referred to as "second pincher drive section") is located on the opposite side to the first pincher drive section 53 with the running path L in between.

The first pincher drive section 53 mainly comprises a rear-end drive plate 531 which pushes the rear end of the pinching rod 511, a rear-end drive source 532 which drives the rear-end drive plate 531, a front-end drive plate 533 which pushes the front end plate 514 of the pinching rod 511 and a front-end drive source 534 which drives the front-end drive plate 533. As shown in FIG. 4, the rear-end drive plate 531 and the front-end drive plate 533 are both provided vertically upright. The rear-end drive plate 531 and the front-end drive plate 533 are held by a guide rod 535. The guide rod 535 extends in the running direction and is held at its front and rear ends by rod holding plates 536. The rod holding plates 536 are secured to both ends of a drive-section holding plate 537 for holding the entire first pincher drive section 53. The guide rod 535 is fitted in holes formed in the rear-end drive plate 531 and the front-end drive plate 533, and guides displacements of the rear-end drive plate 531 and the front-end drive plate 533 along the running direction.

The rear-end drive source 532 and the front-end drive source 534 are linear drive sources, such as air cylinders. When the rear-end drive source 532 is driven, the rear-end drive plate 531 moves forward in the running direction and pushes the rear end of the pinching rod 511. As a result, the pinching rod 511 moves forward against the elasticity of the coil spring 515. This is the state in which the notch of the pinching rod 511 is positioned forward of the movable sleeve 512 as shown in FIG. 3A.

When the front-end drive source 534 is driven, the front-end drive plate 533 pushes the front end plate 514 of the pinching rod 511. Consequently, the end plate 514 is pushed further backward and the long elastic body 2 is cut by the cutter 516 as mentioned above.

The second pincher drive section 54 has almost the same structure as the first pincher drive section 53 except that it does not have portions equivalent to the front-end drive plate 533 and the front-end drive source 534. A rear-end drive plate 541 is displaced by a rear-end drive source 542. The rear-end drive plate 541 is displaced forward and backward while being held and guided by a guide rod 545. The guide rod 545 is held by a pair of rod holding plates 546 which are secured to both ends of a drive-section holding plate 547.

The structure of the rotary mechanism 52 will now be discussed referring to FIGS. 1 and 2. As shown in FIGS. 1 and 2, the aforementioned two pinchers 51 are provided with the holder 3 in between. These two pinchers 51 have the same structure. The rotary mechanism 52 which integrally turns two pinchers 51 mainly comprises a rotary body 521 holding the pinchers 51, torque pins 522 fitted in the rotary body 521, a pin holder 523 holding the torque pins 522, a pulley 524 to which the pin holder 523 is fixed, and a motor 526 which rotates the pulley 524 via a belt 525.

The rotary body 521 is a nearly cylindrical member provided coaxially to the holder 3 as shown in FIG. 2. The holder 3 is located inside the rotary body 521 with a clearance between them.

Fixed to the side face of the rotary body 521 are mounting plates 527 to which the pinchers 51 are respectively mounted. As apparent from FIG. 2, each mounting plate 527 is an L-shaped plate as seen from the top. An opening for mounting the pincher 51 is formed in the mounting plate 527 and the fixed sleeve 513 of the pincher 51 is secured in this opening, thereby mounting the pincher 51 to the mounting plate 527.

Two through holes elongated in the axial direction are formed in the rotary body 521, 180 degrees apart from each other. The torque pins 522 are fitted therein through holes and slightly protrude from the front face of the rotary body 521.

The pin holder 523 which holds the torque pins 522 is a nearly cylindrical member provided at the back of the rotary body 521 and, like the rotary body 521, is coaxial to the holder 3. The rear end of each torque pin 522 is secured to the front end plate of the pin holder 523. The pin holder 523 is held on the base plate via a bearing 520.

The pulley 524, secured to the outer surface of the pin holder 523, is coaxial to the pin holder 523 and the holder 3. Provided below the pulley 524 is an auxiliary pulley 528 which is fixed to the output shaft of the motor 526, with the belt 525 put around the pulley 524 and the auxiliary pulley 528.

As the motor 526 is rotated, the pulley 524 rotates via the auxiliary pulley 528 and the belt 525, causing the torque pins 522 to rotate also via the pin holder 523. Consequently, the rotary body 521 rotates and the pinchers 51 rotate together with the rotation of the rotary body 521. The axis of this rotation coincides with the axis of the holder 3 and therefore coincides with the running path L of the long body 1.

The holder 3 is secured to the base plate 7 by an unillustrated securing member. As shown in FIG. 2, a bearing 31 is provided between the holder 3 and the pin holder 523. Even when the pin holder 523 rotates, therefore, the holder 3 does not turn.

Figure 5:
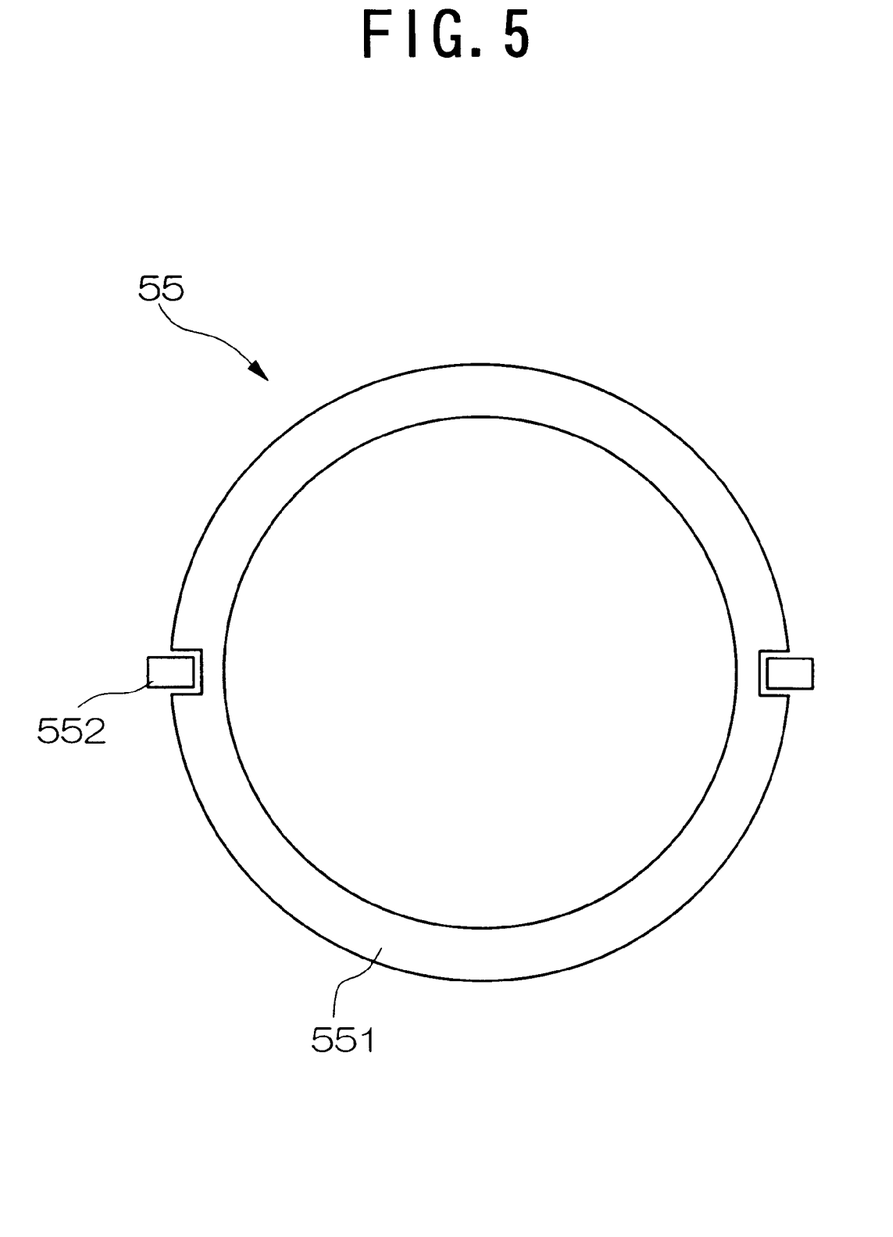
FIG. 5 is a diagram for explaining the structure of an angle detecting unit shown in FIG. 2.

The above-described rotary mechanism 52 has an angle detecting unit 55 for detecting the rotational angle. FIG. 5 is a diagram for explaining the structure of the angle detecting unit 55 shown in FIG. 2. The angle detecting unit 55 mainly comprises a detection plate 551 attached to the rear side of the pulley 524 and a photosensor 552 for detecting the presence of notches formed in the detection plate 551.

As is apparent from FIGS. 2 and 5, the detection plate 551 has a nearly ring shape and two notches are provided 180 degrees apart in the periphery of the detection plate 551. The positions of the notches correspond to the mounted positions of the pair of pinchers 51. The photosensor 552, which is of a transmission type, is provided on a line extending in a direction perpendicular and horizontal to the running path L.

With the photosensor 552 detecting one of the notches in the detection plate 551, the pair of pinchers 51 are positioned on the line that extends in a direction perpendicular and horizontal to the running path L. When the rotary mechanism 52 operates in the above-described manner and the rotary body 521 rotates 180 degrees, the photosensor 552 comes to a state of detecting the other notch. Under this situation, the pair of pinchers 51 should have switched their positions with each other. The angle detection unit 55 monitors every 180-degree rotation of the rotary body 521 in this manner.

The structure of the elastic-body feeding mechanism 6 which feeds the long elastic body 2 to the winding mechanism 5 will now be described referring to FIGS. 1 and 2. In this embodiment, an elastic cord of a predetermined length is used as a line-like elastic body. Therefore, the long elastic body 2 is an elastic cord significantly longer than the line-like elastic body. The elastic-body feeding mechanism 6 mainly comprises a bobbin 61 around which such a long elastic body 2 is wound, two guide cylinders 62 for guiding the long elastic body 2 drawn out of the bobbin 61, a guide pulley 63 provided between the two guide cylinders 62 and a tension pulley 64 provided on the feeding path for the long elastic body 2 from the guide cylinders 62 to the pinchers 51.

The tension pulley 64 imparts predetermined tension to the long elastic body 2 to be fed to the pinchers 51. An adequate frictional force is produced on the surface of the tension pulley 64 which the long elastic body 2 contacts. Connected to the tension pulley 64 is the output shaft of a torque motor 65 which generates the torque that interferes with the rotation of the output shaft and can be adjusted. The torque motor 65 uses two magnets whose magnetic forces generate the torque. By adjusting the torque generated by the torque motor 65, the tension on the long elastic body 2 to be fed to the pinchers 51 is adjusted.

A gathering rod 66 is provided on the feeding path for the long elastic body 2 between the tension pulley 64 and the pinchers 51 as shown in FIGS. 1 and 2. As shown in FIG. 2, the gathering rod 66 extends in a direction perpendicular and horizontal to the running direction. The gathering rod 66 is held on a rod holder 661 to which a gathering-rod drive source 662 like a control cylinder is connected. When the gathering-rod drive source 662 is driven, the gathering rod 66 moves in the running direction.

Referring now to FIGS. 6 through 9, the winding of the long elastic body 2 by the winding mechanism 5 will be explained. FIGS. 6 to 9 are diagrams for explaining the winding of the long elastic body 2 by the winding mechanism 5; FIGS. 6A, 7A, 8A and 9A are front views, and FIGS. 6B, 7B, 8B and 9B are side views.

Figure 6A:
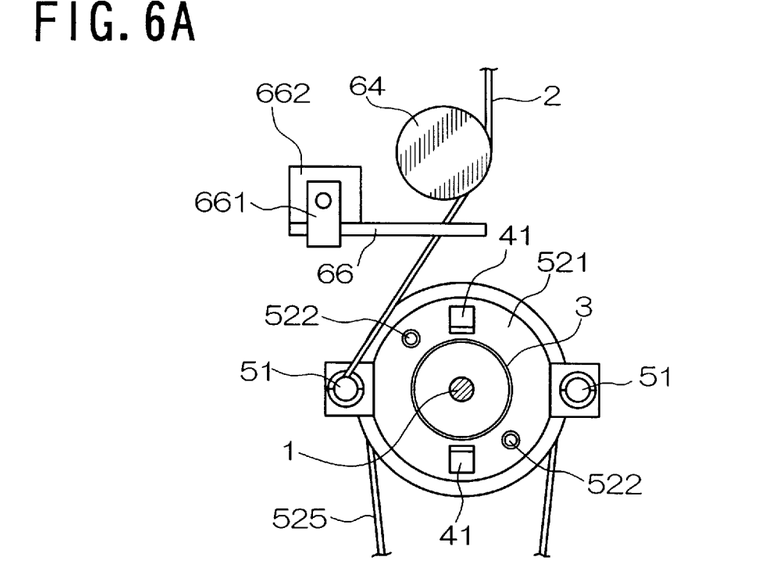
FIG. 6A is a front view for explaining the winding of the long elastic body by the winding mechanism.
Figure 6B:
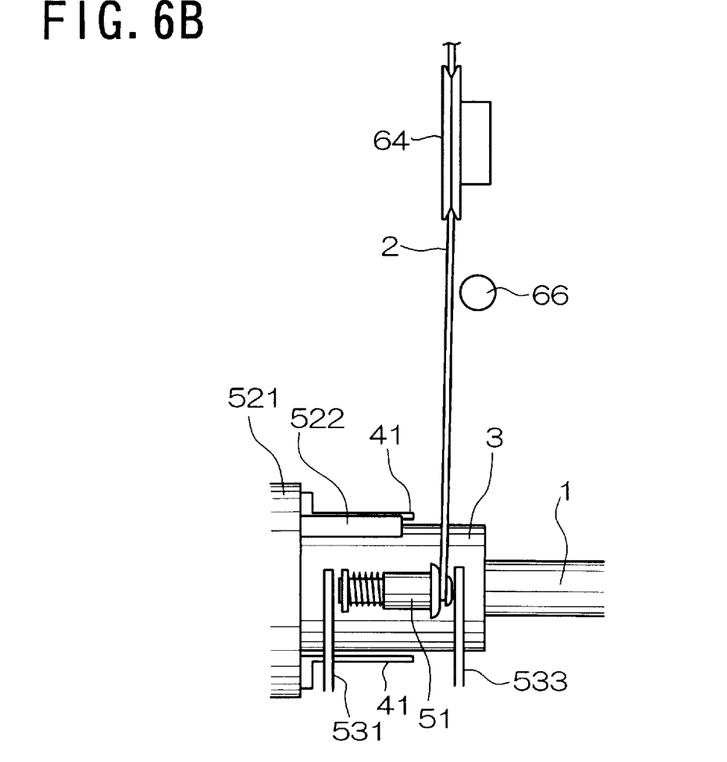
FIG. 6B is a side view for explaining the winding of the long elastic body by the winding mechanism.
Figure 7A:
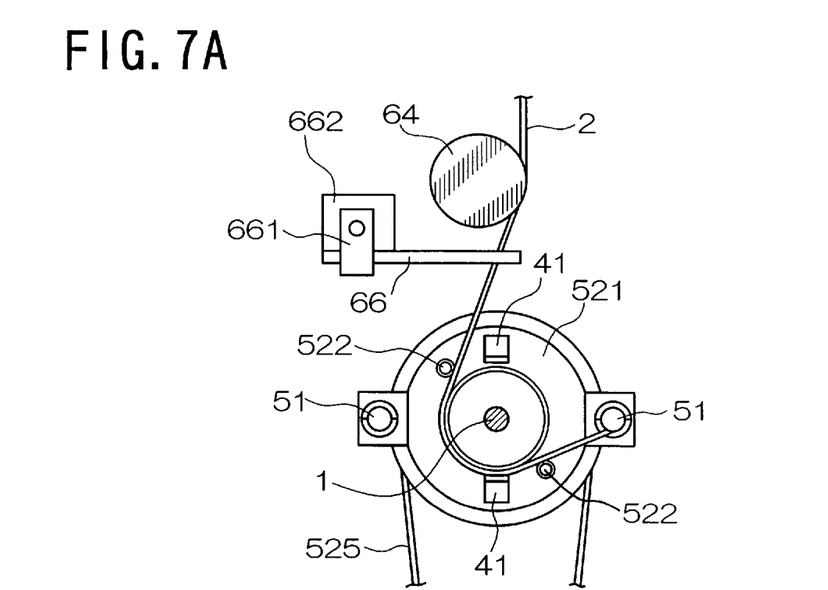
FIG. 7A is a front view for explaining the winding of the long elastic body by the winding mechanism.
Figure 7B:
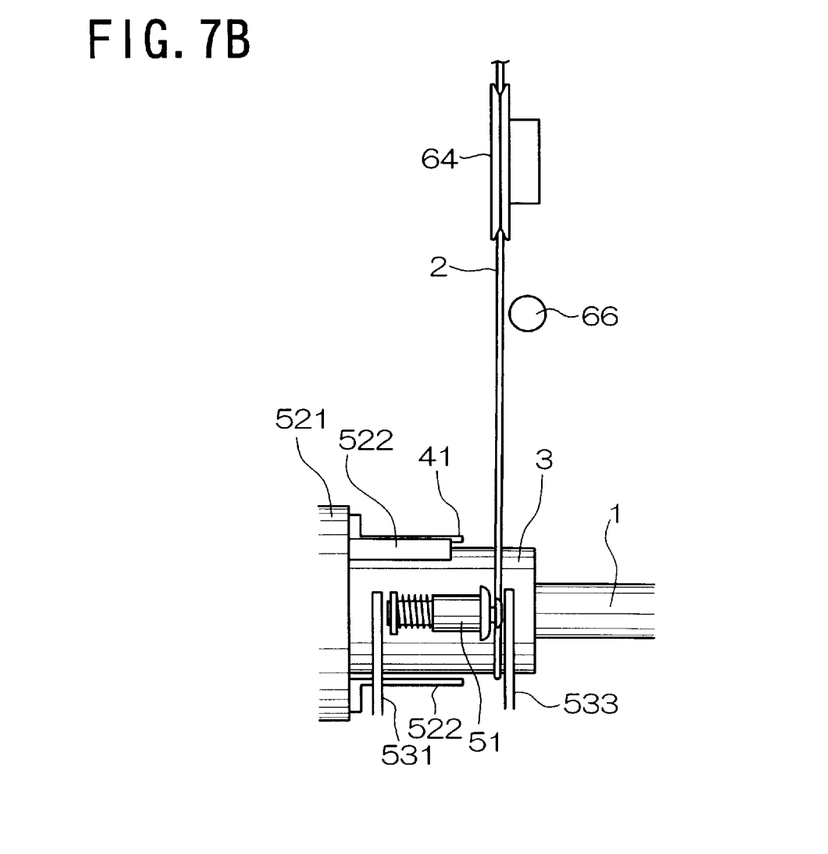
FIG. 7B is a side view for explaining the winding of the long elastic body by the winding mechanism.

When the rotary mechanism 52 operates with the distal end of the long elastic body 2 held by one pincher 51 as shown in FIGS. 6A and 6B, the pair of pinchers 51 rotates together. When pair the pinchers 51 rotate 180 degrees, the position of one pincher 51 and the position of the other pincher 51 are changed with each other, as shown in FIG. 7A. At this time, the rear-end drive source 532 of the first pincher drive section 53 is not in operation as shown in FIG. 7B, so that the pinching rod 511 of the other pincher 51 is not displaced forward. That is, the long elastic body 2 is not held yet by the other pincher 51 at this time. As shown in FIG. 7A, therefore, the long elastic body 2 is in contact with the left-hand side face of the holder 3 and is hooked there while its distal end is being held by said one pincher 51 located on the right-hand side.

Figure 8A:
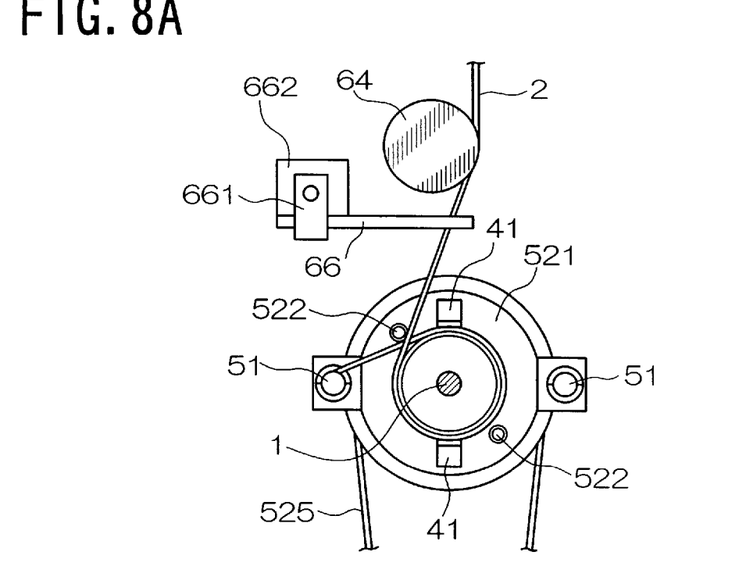
FIG. 8A is a front view for explaining the winding of the long elastic body by the winding mechanism.
Figure 8B:
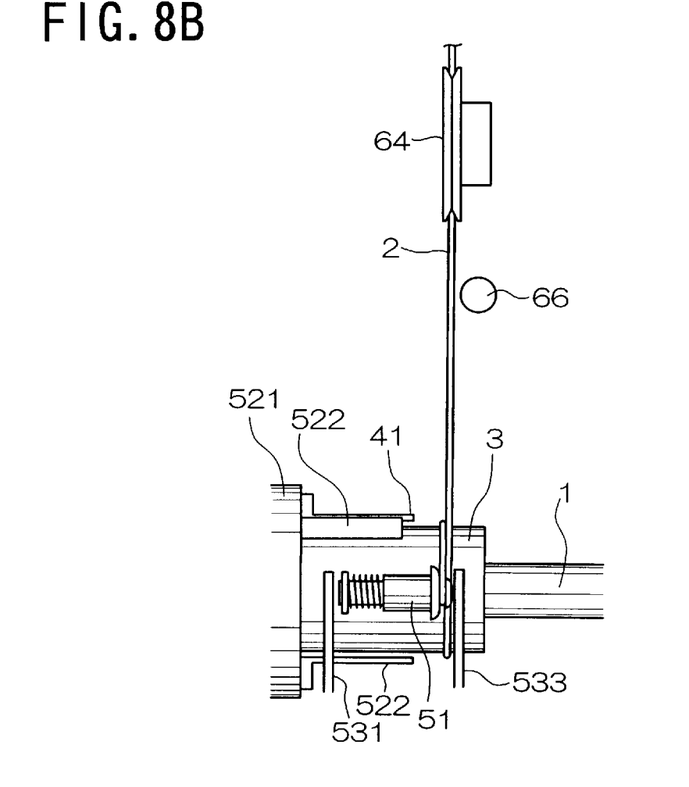
FIG. 8B is a side view for explaining the winding of the long elastic body by the winding mechanism.

When the pinchers 51 are further rotated 180 degrees and the position of said one pincher 51 and the position of the other pincher 51 are changed with each other, the long elastic body 2 is wound around the holder 3 by nearly one turn while its distal end is being held by said one pincher 51 located on the left-hand side as shown in FIG. 8A. At this time, the tension pulley 64 is positioned slightly rearward of the holding position of the pincher 51 as shown in FIG. 8B. Therefore, the long elastic body 2 wound by one turn does not have any overlapping portion.

Figure 9A:
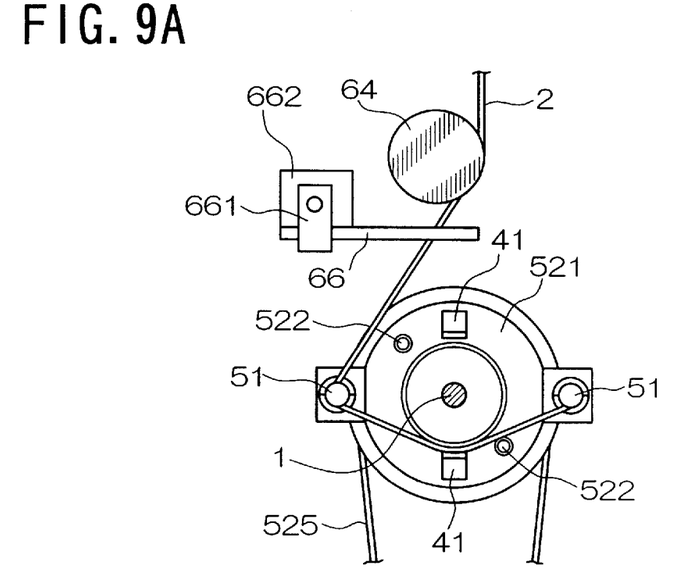
FIG. 9A is a front view for explaining the winding of the long elastic body by the winding mechanism.
Figure 9B:
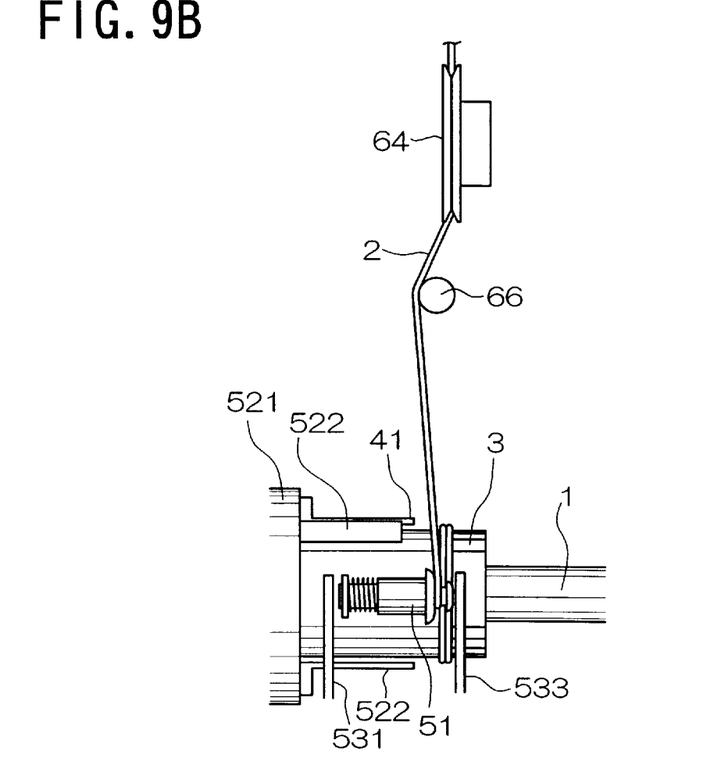
FIG. 9B is a side view for explaining the winding of the long elastic body by the winding mechanism.

When the pinchers 51 are further rotated 180 degrees from the above state to the state shown in FIGS. 9A and 9B, the winding operation is completed. At this time, the gathering-rod drive source 662 and the rear-end drive source 532 are activated to cause the other pincher 51 to hold the long elastic body 2. That is, as shown in FIG. 9B, the gathering rod 66 is slightly displaced rearward and the other pincher 51 is rotated to the left-hand position from the upper position. When the other pincher 51 is moved to the left-hand position, the rear-end drive source 532 is driven to move the pinching rod 511 forward against the elasticity of the coil spring 515. This causes the long elastic body 2 to be positioned at the notch of that pinching rod 511 as shown in FIG. 3A. When the rear-end drive source 532 drives the rear-end drive plate 531 in the reverse direction in the above state, the pinching rod 511 is moved backward by the elasticity of the coil spring 515, causing the long elastic body 2 to be held by the other pincher 51.

As is apparent from the above description, the rotary mechanism 52 rotates the rotary body 521 900 degrees (two turns and a half) from the state shown in FIGS. 6A and 6B. Therefore, the winding mechanism 5 winds the long elastic body 2 on the holder 3 by two turns. As mentioned above, the angle detection unit 55 monitors the above-described rotation every 180 degrees.

The structure of the entwining mechanism 4 will now be described referring to FIGS. 1, 2 and 4. The entwining mechanism mainly comprises two contact pins 41 (freeing mechanisms) which contact the wound long elastic body 2 and a linear motion mechanism 42 which moves the contact pins 41 linearly.

The contact pins 41, as shown in FIG. 2, extend in the running direction and are respectively located above and below the holder 3. The rear end of each contact pin 41 is bent and this portion is secured to the front face of the rotary body 521. The surface of the contact pin 41 on the side of the running path L is where the wound long elastic body 2 contacts, and this surface (hereinafter called the "contact surface") is formed from a material which produces a large frictional force, such as rubber.

The linear motion mechanism 42 is designed to move linearly the rotary body 521 to which the contact pins 41 are fixed. The linear motion mechanism 42 mainly comprises a pair of rollers 421 fitted in the rotary body 521 and an entwining drive source 422 which linearly moves the rotary body 521 via the rollers 421.

The rotary body 521, as shown in FIG. 4, has a flange portion in which a recess having bracket-shaped cross section is formed. The pair of rollers 421 are fitted in this recess. The pair of rollers 421 face with each other on a horizontal plane with the running path L in between.

The pair of rollers 421 are respectively secured to the drive-section holding plates 537 and 547 of the first and second pincher drive sections 53 and 54. Both drive-section holding plates 537 and 547 are supported by a support 43 whose lower end is fixed to a movable plate 44. The movable plate 44, which extends vertically and horizontally to the running direction, is mounted over linear guides 45. The output shaft, 423, of the entwining drive source 422 is attached to the movable plate 44 via a shaft mounting plate 46. The entwining drive source 422 is a linear drive source like a control cylinder or a servomotor or the like equipped with a ball screw, and linearly moves the movable plate 44 in the running direction. As the movable plate 44 moves, the rollers 421 move via the support 43 and the drive-section holding plate 537, and pushes the rotary body 521. As a result, the rotary body 521 moves together with the contact pins 41.

Figure 10A:
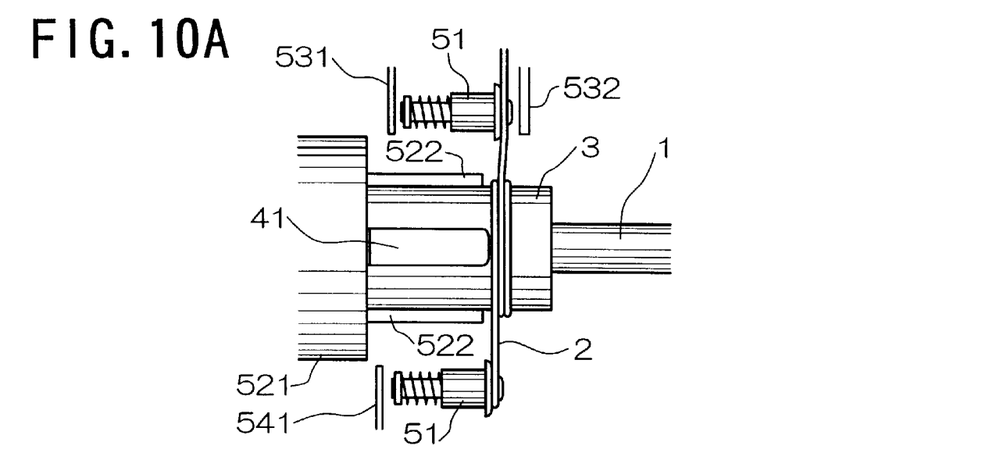
FIG. 10A is a plan view for explaining entwining by the entwining mechanism which is seen from below at the stage before the long elastic body is entwined.
Figure 10B:
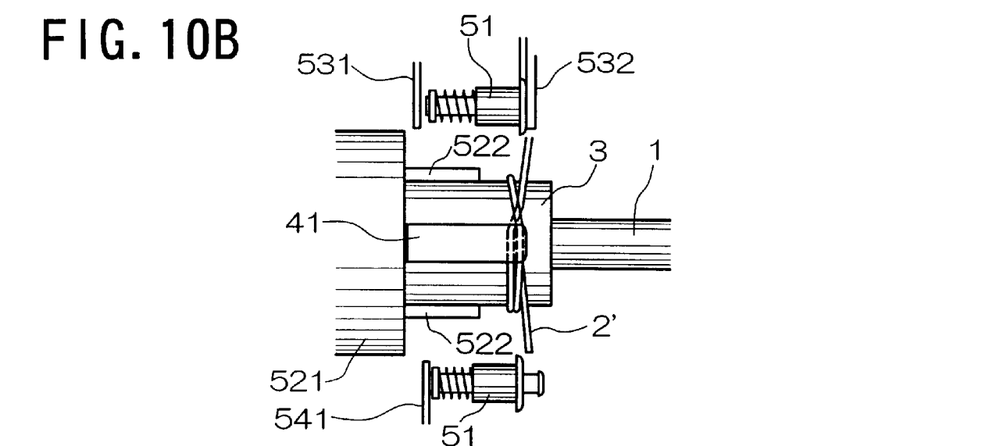
FIG. 10B is a plan view for explaining entwining by the entwining mechanism which is seen from below at the stage that the long elastic body is entwined.
Figure 10C:
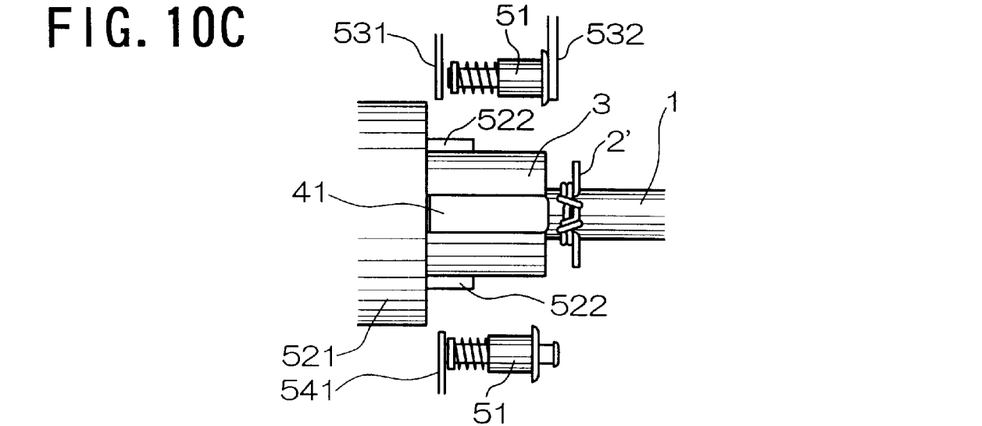
FIG. 10C is a plan view for explaining entwining by the entwining mechanism which is seen from below at the stage that the line-like elastic body is entwined on the long body.

Entwining by the above-described entwining mechanism 4 will be discussed below referring to FIGS. 10A to 10C. FIGS. 10A to 10C are the plan views for explaining entwining by the entwining mechanism which are seen from below.

FIG. 10A shows winding by the winding mechanism 5 that has completed. In this situation, the entwining drive source 422 is activated to move the contact pins 41 forward as mentioned above. This forward movement causes the contact surfaces of the contact pins 41 to contact the long elastic body 2. When the contact pins 41 further move forward, the long elastic body 2 is caught by the frictional force on the contact surfaces of the contact pins 41, so that the long elastic body 2 is entwined as shown in FIG. 10B. At this time, as described earlier, the front-end drive source 534 of the first pincher drive section 53 is activated to cause the long elastic body 2 to be cut by the cutter 516, producing a line-like elastic body 2' from the long elastic body 2. At the same time, the rear-end drive source 542 of the second pincher drive section 54 is activated to move the rear-end drive plate 541 forward. This frees the distal end of the line-like elastic body 2' from the pincher 51.

When the entwining drive source 422 is activated to move the contact pins 41 forward by a predetermined distance, the contact pins 41 cause the entwined line-like elastic body 2' to slide on the surface of the holder 3. When the line-like elastic body 2' slides beyond the edge of the distal end of the holder 3, it makes rapid contact due to its own elasticity and is entwined on the long body 1 as shown in FIG. 10C.

The general operation of the defective-portion marking apparatus with the above-described structure will be described, discussing also the defective-portion marking method according to this invention. The defective-portion marking apparatus with the above-described structure is used together with a defective-portion detecting apparatus (not shown) which detects defective portions on the long body 1 and a control section (not shown) which controls the defective-portion marking apparatus in accordance with signals from the defective-portion detecting apparatus.

As mentioned above, the long elastic body 2 should be wound around the holder 3 by activating the winding mechanism 5 and the line-like elastic body 2' should be entwined on the holder 3 by activating the entwining mechanism 4 (the state shown in FIG. 10B). This is the standby state. When the defective-portion detecting apparatus detects a defective portion in this state, it sends a signal to the control section. In response to this signal, the control section sends a drive signal (hereinafter called "marking signal") to the defective-portion marking apparatus. This marking signal activates the entwining drive source 422 to further move the contact pins 41 forward, causing the line-like elastic body 2' to be entwined on the long body 1 as shown in FIG. 10C.

The defective-portion detecting apparatus is provided on the running path L at the back of the defective-portion marking apparatus. The long body 1 is running at a controlled velocity, and the marking signal is sent at the timing at which the detected defective portion reaches the edge of the distal end of the holder 3 of the defective-portion marking apparatus. Therefore, the line-like elastic body 2' is entwined at the detected defective portion or in the vicinity thereof.

The above-described defective-portion marking method and defective-portion marking apparatus according to this embodiment have the following advantages over the prior art.

First, as the line-like elastic body 2' is wound on the long body 1, a marking can be made on the outer surface of the long body 1 over 360 degrees. Therefore, the marked portion is reliably detected and is not missed. The wound line-like elastic body 2' can easily be separated from the long body 1 by pulling one end of the line-like elastic body 2'. If a marking is made erroneously, therefore, it can be corrected easily.

Further, unlike in the ink spraying method and the seal attaching method, it is not difficult to make a marking when the long body is running quickly. Furthermore, the material for the base long body 1 or its surface condition limits some cases to the ink spraying method or the seal sticking method, whereas this embodiment does not suffer such a restriction and can make a marking on the long body 1 of any material or with any surface condition. When the surface of the long body 1 is a mirror or the like, the line-like elastic body 2' may slip around, but this does not raise a practical problem if the elasticity of the line-like elastic body 2' is increased.

Since a marking is made by entwining the line-like elastic body 2', not making the line-like elastic body 2' into a rink shape by joining both ends thereof, the conventional problems of enlarging the apparatus and taking into consideration the strength of the joined portion do not arise. Because the wound line-like elastic body 2' can easily be separated from the long body 1 by pulling one end of the line-like elastic body 2', a work of removing the marking is considerably easier than the one in a case of a ring-like elastic body.

It is important that the winding mechanism 5 winds the long elastic body 2 on the holder 3 by two turns using the above-described structure of this embodiment in order to sufficiently entwine the line-like elastic body 2' on the long body 1. Entwining the long elastic body 2, wound on the holder 3 by two turns, with the contact pins 41 makes the entwining complicated so that the line-like elastic body 2', when entwined on the long body 1, is complexly entwined and will not be unentwined easily. Winding by less than two turns, e.g., one and half turns, entwining becomes rather simple and application of some shocks may unravel the line-like elastic body 2'. Even when entwining is made by winding the line-like elastic body 2' by two turns, the line-like elastic body 2' can be easily unraveled by a human hand by simply pulling one end of the line-like elastic body 2'. It is to be noted that in principle, the winding mechanism 5 has only to make turns greater than one turn (360 degrees). If the long elastic body 2 wound on the long body 2' has any overlapping portion, a marking can be made on the long body 1 by entwining the overlapped portion.

The structure for cutting the long elastic body 2 into the line-like elastic body 2' also is significant in making the marking apparatus more practical. For example, according to the marking apparatus of this invention, it is possible to prepare multiple line-like elastic bodies 2' and make a marking by using then one by one. This structure however requires the troublesome work of cutting the long elastic body 2 into multiple line-like elastic bodies 2' in advance. Further, the mechanism of taking out the prepared line-like elastic bodies 2' one by one and holding both of its ends is complex and is not easy to design. In view of the above, the structure of the marking apparatus of this invention to cut the long elastic body 2 at a predetermined length to provide the line-like elastic body 2' is significantly practical.

In principle, the long elastic body 2 should have a length at least double the length of the line-like elastic body 2'. It is however preferable that the long elastic body 2 with a longer length should be wound on the bobbin 61 so that frequent replacement of the bobbin 61 can be avoided.

In the above-described defective-portion marking method and defective-portion marking apparatus of this embodiment, various kinds of long bodies besides the above-discussed electric wires can be used for the long body 1. Such long bodies may include cables, optical fibers, pipes or hoses of rubber or plastic, various kinds of pipes like a water pipe or gas pipe, and steel products having shapes of a round rod and a square rod, which are to be used for various purposes. Furthermore, the line-like elastic body 2' may be made of various kinds of elastic materials, such as natural rubber of thermoplastic elastomer.

Although the long body 2 is cut into the line-like elastic body 2' after it is wound on the holder 3 in this embodiment, it may be cut into the line-like elastic body 2' before being wound on the holder 3. It is not essential that the pincher 51 is provided with the cutter 516, and a cutting member may be provided separately from the pincher 51. But, providing the pincher 51 with the cutter 516 can provide a structure which can both hold and cut the long elastic body 2, thus simplifying the mechanism of the apparatus.

The cross section of the long body 1 is not limited to a circular shape, but may have other shapes like an oval shape and a rectangular shape. The holder 3 is not limited to a round cylinder but may take the shape of a square cylinder. The shape of the holder 3 is not limited to a cylinder as long as it can hold the line-like elastic body 2' entwined in a circle; for example, the holder 3 may be designed to have a plurality of hooks on which the line-like elastic body 2' is to be hooked and held.

The technique of this invention can be adapted to a case of making marks for other purposes than marking defective portions as well as a case of marking defective portions. For example, the above-described marking apparatus can be used to put marks on the long body 1 at predetermined intervals to indicate where the long body 1 is to be cut. In this case, while marking is carried out at predetermined intervals, defective portions when detected are also marked.

A description will now be given of a bundling apparatus according to another embodiment of this invention.

The above-described structure of the marking apparatus can be adapted as it is to a bundling apparatus. For example, the bundling apparatus of this invention can be used to bundle flowers in a flower shop or the like. In this case, a long body should be the stem of a flower. Specifically, the stem portions of a plurality of flows are aligned and are inserted a little in the holder 3 from the front opening of the holder 3 shown in FIG. 2. Then, the line-like elastic body 2' entwined on the holder 3 is moved forward as discussed in the foregoing description to be entwined around the bundle of the stems and bundle them together.

Bundling this way can allow the line-like elastic body 2' to be separated by simply pulling one end of the line-like elastic body 2' as in the case of the previous embodiment, so that unbundling becomes easier. The removed line-like elastic body 2' can be used again if needed. The technique of this invention can be used to bundle various kinds of products, such as long vegetables, such as asparagus.

EXAMPLES

Examples of the above-described marking method and marking apparatus will now be discussed. The following description will given of a case where an electric wire with an outside diameter of about 30 mm is used as the long body 1 and defective portions like a scratch or crack on the surface of this electric wire is to be marked.

Synthetic rubber essentially consisting of 25% by weight of styrene and 75% by weight of butadiene was used for the long elastic body 2 whose thickness was set to about 1.5 mm. This long elastic body 2 was stretched by 400 to 500% and entwined on the holder 3 as the line-like elastic body 2' by the winding mechanism 5 and the entwining mechanism 4.

The long body 1 was permitted to run at a velocity of 600 mm/min and the defective-portion detecting apparatus using scattered laser light was used to detect a defective portion. This distance between the position where the defective portion was detected and the entwining position of the line-like elastic body 2' was about 1 meter, so that the marking signal was sent with a time lag of about 100 milliseconds upon reception of the signal indicating the detection of the defective portion and the line-like elastic body 2' was entwined around the long body 1. As a result, the line-like elastic body 2' could be reliably wound around the long body 1 or the electric wire at the defective portion, thus marking the defective portion.

What is claimed is:

1. A defective-portion marking method for marking a defective portion of a long body, comprising the steps of:

holding a line-like elastic body having a free length shorter than a circumference of said long body in an entwined state in such a way that said line-like elastic body forms a turn greater than said circumference of said long body; and then releasing said line-like elastic body to permit said line-like elastic body to contract by the elasticity thereof, thereby entwining and winding said line-like elastic body around said long body at a defective portion or in a vicinity thereof.

2. A defective-portion marking apparatus for marking a defective portion of a long body which runs in a lengthwise direction thereof, comprising:

a holder for holding a line-like elastic body having a free length shorter than a circumference of said long body in an entwined state in such a way that said line-like elastic body forms a turn greater than said circumference of said long body; and an entwining mechanism for freeing said line-like elastic body of holding by said holder to permit said line-like elastic body to contract by the elasticity thereof, thereby entwining and winding said line-like elastic body around said long body at a defective portion or in a vicinity thereof.

3. The defective-portion marking apparatus according to claim 2, further comprising:

a cutter for cutting a long elastic body whose length is twice a length of said line-like elastic body or greater at a predetermined length, providing said line-like elastic body; and an elastic-body feeding mechanism for feeding said long elastic body to said cutter.

4. The defective-portion marking apparatus according to claim 2, wherein said holder holds said line-like elastic body stretched in one or more turns along a circumference greater than said circumference of said long body.

5. A bundling apparatus for bundling a plurality of long bodies, comprising:

a holder for holding a line-like elastic body having a free length shorter than a circumference of a bundle of a plurality of long bodies in an entwined state in such a way that said line-like elastic body forms a turn greater than said circumference of said bundle of long bodies; and a freeing mechanism for freeing said like-like elastic body of holding by said holder to permit said line-like elastic body to contract by the elasticity thereof, thereby winding said line-like elastic body around said bundle of long bodies.

* * * * *